(12) United States Patent
Fulton et al.

(10) Patent No.: US 7,309,566 B2
(45) Date of Patent: Dec. 18, 2007

(54) GENETICALLY BIOTINYLATED RECOMBINANT ANTIBODY IN IMMUNOFILTRATION ASSAY BY LIGHT ADDRESSABLE POTENTIOMETRIC SENSOR FOR IDENTIFICATION OF VENEZUELAN EQUINE ENCEPHALITIS VIRUS

(75) Inventors: R. Elaine Fulton, Medicine Hat (CA); Leslie P. Nagata, Medicine Hat (CA); Azhar Z. Alvi, Mississauga (CA); Weigang Hu, Medicine Hat (CA)

(73) Assignee: Her Majesty the Queen in right of Canada, as represented by the Minister of National Defense, Ontario (CA)

( * ) Notice: Subject to any disclaimer, the term of this patent is extended or adjusted under 35 U.S.C. 154(b) by 155 days.

(21) Appl. No.: 10/807,194

(22) Filed: Mar. 24, 2004

(65) Prior Publication Data

US 2004/0229216 A1    Nov. 18, 2004

Related U.S. Application Data

(60) Provisional application No. 60/456,939, filed on Mar. 25, 2003.

(51) Int. Cl.
| | |
|---|---|
| *C07K 16/10* | (2006.01) |
| *C07K 16/08* | (2006.01) |
| *G01N 33/543* | (2006.01) |
| *G01N 33/569* | (2006.01) |
| *C12Q 1/70* | (2006.01) |

(52) U.S. Cl. ...................................................... 435/5
(58) Field of Classification Search ............ 424/218.1, 424/132.1; 435/5, 6, 7.1, 252.3, 7.23
See application file for complete search history.

(56) References Cited

OTHER PUBLICATIONS

Hu et al., "Genetic Engineering of Streptavidin-Binding Peptide Tagged Single-Chain Variable Fragment Antibody to Venezuelan Equine Encephalitis Virus," Hybridoma and Hybridomics, vol. 21, No. 6, pp. 415-420, Mary Ann Liebert, Inc. (2002).
Lee et al., "Rapid Immunofiltration Assay of Newcastle Disease Virus Using a Silicon Sensor," Journal of Immunological Methods, vol. 166, pp. 123-131, Elsevier Science Publishers, B.V. (1993).
Luo et al., "Expression of a Fusion Protein of scFv—Biotin Mimetic Peptide for Immunoassay," Journal of Biotechnology, vol. 65, pp. 225-228, Elsevier Science B.V. (1998).
Emanuel et al., "Recombinant Antibodies: A New Reagent for Biological Agent Detection," Biosensors & Bioelectronics, vol. 14, pp. 751-759, Elsevier Science S.A. (2000).

*Primary Examiner*—Bruce R. Campell
*Assistant Examiner*—M. Franco Salvoza
(74) *Attorney, Agent, or Firm*—Rader, Fishman & Grauer, PLLC

(57) ABSTRACT

A genetically biotinylated single chain fragment variable (scFv) antibody against Venezuelan equine encephalitis virus (VEE) being applied in a system consisting of an immunofiltration-enzyme assay (IFA) with a light addressable potentiometric sensor (LAPS) for the rapid identification of VEE is disclosed. The IFA entails formation of an immunocomplex sandwich consisting of VEE, biotinylated antibody, fluoresceinated antibody and streptavidin, capturing the sandwich by filtration on biotinylated membrane, and detecting the sandwich by anti-fluorescein urease conjugate. The concentration ratio of biotinylated to fluoresceinated antibodies is investigated and optimized. The IFA/LAPS assay sensitivity was approximately equal to that of a conventional enzyme-linked immunosorbant assay utilizing polystyrene plates and a chromogenic substrate, however, less time and effort were required for performance of the IFA/LAPS assay.

5 Claims, 3 Drawing Sheets

Fig.2

GENETICALLY BIOTINYLATED RECOMBINANT ANTIBODY IN IMMUNOFILTRATION ASSAY BY LIGHT ADDRESSABLE POTENTIOMETRIC SENSOR FOR IDENTIFICATION OF VENEZUELAN EQUINE ENCEPHALITIS VIRUS

This Application claims the benefit of U.S. Provisional Application No. 60/456,939, filed on Mar. 25, 2003, the entire content of which is incorporated by reference in this application.

FIELD OF THE INVENTION

This invention relates to the construction of a genetically biotinylated single chain fragment variable (scFv) antibody against Venezuelan equine encephalitis virus (VEE) being applied in a system consisting of an immunofiltration-enzyme assay (IFA) with a light addressable potentiometric sensor (LAPS) for the rapid identification of VEE. The IFA/LAPS assay averts the conventional method of employing antibodies which were biotinylated chemically.

BACKGROUND OF THE INVENTION

List of Prior Art Literatures

Johnson, K. M., Shelokov, A., Peralta, P. H., Dammin, G. J., and Young, N. A. (1968) Recovery of Venezuelan equine encephalomyelitis virus in Panama. A fatal case in man. *Am. J. Trop. Med. Hyg.* 17, 432-440.

Franck, P. T., and Johnson, K. M. (1970) An outbreak of Venezuelan encephalitis in man in the Panama Canal Zone. *Am. J. Trop. Med. Hyg.* 19, 860-865.

Johnston, R. E., and Peters, C. J. (1996) Alphavirus. in *Fields virology*, $3^{rd}$ ed. (Fields, B. N., Knipe, D. M. and Howley, P. M., Eds.), pp.843-898, Raven Publishers, Philadelphia, Pa.

Christopher, G. W., Cieslak, T. J., Pavlin, J. A., and Eitzen, E. M. Jr. (1997) Biological warfare. A historical perspective. *JAMA*. 278, 412-417.

Blendon, R. J., Benson, J. M., DesRoches, C. M., Pollard, W. E., Parvanta, C., and Herrmann, M. J. (2002) The impact of anthrax attacks on the American public. *MedGenMed*. 4,1-8.

Libby, J. M., and Wada, H. G. (1989) Detection of Neisseria meningitidis and Yersinia pestis with a novel silicon-based sensor. *J. Clin. Microbiol.* 27,1456-1459.

Lee, W. E., Thompson, H. G., Hall, J. G., Fulton, R. E., and Wong, J. P. (1993) Rapid immunofiltration assay of Newcastle disease virus using a silicon sensor. *J. Immunol. Methods*. 166,123-131.

Gehring, A,G, Patterson, D. L., and Tu, S. I. (1998) Use of a light-addressable potentiometric sensor for the detection of *Escherichia coli* O157:H7. *Anal. Biochem.* 258, 293-298

Lee, W. E., Thompson, H. G., Hall, J. G., and Bader, D. E. (2000) Rapid detection and identification of biological and chemical agents by immunoassay, gene probe assay and enzyme inhibition using a silicon-based biosensor. *Biosens. Bioelectron.* 14, 795-804.

Carlson, M. A., Bargeron, C. B., Benson, R. C., Fraser, A. B., Phillips, T. E., Velky, J. T., Groopman, J. D., Strickland, P. T., and Ko, H. W. (2000) An automated, handheld biosensor for aflatoxin. *Biosens. Bioelectron.* 14, 841-848.

Emanuel, P. A., Dang, J., Gebhardt, J. S., Aldrich, J., Garber, E. A., Kulaga, H., Stopa, P., Valdes, J. J., and Dion-Schultz, A. (2000) Recombinant antibodies: a new reagent for biological agent detection. *Biosens. Bioelectron.* 14, 751-759.

Roehrig, J. T., and Mathews, J. H. (1985) The neutralization site on the E2 glycoprotein of Venezuelan equine encephalomyelitis (TC-83) virus is composed of multiple conformationally stable epitopes. *Virology* 142, 347-356

Miralles, F., Takeda, Y., and Escribano, M. J. (1991) Comparison of carbohydrate and peptide biotinylation on the immunological activity of IgG1 murine monoclonal antibodies. *J. Immunol. Methods* 140, 191-196.

Hu, W. G., Alvi, A. Z., Fulton, R. E., Suresh, M. R., and Nagata, L. P. (2002) Genetic engineering of streptavidin-binding peptide tagged single-chain variable fragment antibody to Venezuelan equine encephalitis virus. *Hybridoma & Hybridomics* 21, 415-420.

Huston, J. S., Levinson, D., Mudgett-Hunter, M., Tai, M. S., Novotny, J., Margolies, M. N., Ridge, R. J., Bruccoleri, R. E., Haber, E., and Crea, R. (1988) Protein engineering of antibody binding sites: recovery of specific activity in an anti-digoxin single-chain Fv analogue produced in *Escherichia coli. Proc. Natl. Acad. Sci. USA.* 85, 5879-5883.

Marin, M., Brockly, F., Noel, D., Etienne-Julan, M., Biard-Piechaczyk, M., Hua, T. D., Gu, Z. J., and Piechaczyk, M. (1995) Cloning and expression of a single-chain antibody fragment specific for a monomorphic determinant of class I molecules of the human major histocompatibility complex. *Hybridoma* 14, 443-451.

Bruyns, A. M., De Jaeger, G., De Neve, M., De Wilde, C., Van Montagu, M., and Depicker, A. (1996) Bacterial and plant-produced scFv proteins have similar antigen-binding properties. *FEBS Lett.* 386, 5-10.

Luo, D., Geng, M., Schultes, B., Ma, J., Xu, D. Z., Hamza, N., Qi, W., Noujaim, A. A., and Madiyalakan, R. (1998) Expression of a fusion protein of scFv-biotin mimetic peptide for immunoassay. *J. Biotechnol.* 65, 225-228.

Venezuelan equine encephalitis virus (VEE), belonging to alphavirus genus of the family *Togaviridae*, is associated with encephalitis (Johnson et al., 1968; Franck et al., 1970). Although natural infection with this virus results from mosquito bites, the virus is also highly infectious by aerosol (Johnston et al., 1996). Thus, VEE is a potential biological warfare/bioterrorist (BW/BT) agent of concern. The use of biological agents as BW/BT weapons is not a new concept, and alleged uses of biological agents as military or terrorist weapons can be found throughout history (Christopher et al., 1997). The most recent case of use of the biological agent, anthrax, as a bioterrorist agent occurred in USA in 2001 (Blendon et al., 2002). Identification of biological agents involves either finding the agent in the environment or medical diagnosis of the agent and/or its effect(s) on human or animal victims. Early and rapid detection and identification of a biological agent is crucial for immediate and specific treatment of affected individuals and in order to limit the epidemic spread of associated disease.

Antibodies are critical reagents used in several biodetection platforms for the identification of biological agents (Libby et al., 1989; Lee et al., 1993; Gehring et al., 1998; Lee et al., 2000; Carlson et al., 2000; Emanuel et al., 2000). Monoclonal antibody (mAb) 1A4A1 is specific for an envelope glycoprotein of VEE. This MAb has been shown to be highly reactive to VEE (Roehrig et al., 1985). Single chain variable fragment (scFv) mAbs are comprised of variable regions of heavy and light chains of immunoglobulin, covalently connected by a peptide linker (Huston et al., 1988). These small proteins generally retain the specificity and affinity for antigen similar to their parental mAbs and possibly bind to poorly accessible epitopes more efficiently due to their small size (Marin et al., 1995; Bruyns et al., 1996). The attractiveness of scFv antibodies is that they can be produced economically and stably in bacteria and can be manipulated via genetic engineering for different purposes, such as biotinylation (Luo et al., 1998). Recently, an anti-VEE mA116 scFv Ab was cloned from 1A4A1 MAb "as taught in U.S. patent application Ser. No. 10/096,246, now U.S. Pat. No. 6,818.748, herein incorporated by reference". This scFv showed an affinity to VEE comparable to that of the parental 1A4A1 MAb and therefore is a good candidate as immunodiagnostic reagent.

Previously, a flow-through immunofiltration-enzyme assay (IFA) in conjunction with a light addressable potentiometric sensor (LAPS) has been used for identification of microbial agents (Libby et al., 1989; Lee et al., 1993; Gehring et al., 1998; Lee et al., 2000). However, the IFA/LAPS system described to date utilized biotin-streptavidin-mediated capture filtration of immunocomplexes in which one of the analyte-specific antibodies required chemical biotinylation. The process of chemical biotinylation is commonly associated with impairment of the antigen-binding site on the antibody. Other disadvantages of chemically biotinylating mAbs as immunodiagnostic reagents include the cost and time required for growth and maintenance of hybridoma cell lines and production and purification of mAbs, and the potential for the occurrence of genetic mutation during repeated cycles of cell growth, rendering routine production of mAbs from hybridoma cell lines difficult, expensive, and time-consuming. Chemical biotinylation of antibodies is also time-consuming. Most biotins bind to amino groups on proteins and the degree of labeling tends to differ from batch to batch. The possibility also exists that the biological activity of the antibody may be negatively affected by the labeling procedure (Miralles et al., 1991).

Accordingly, it is desirable to eliminate the need for chemical biotinylation. In US Provisional Application No. 60/448,902 submitted earlier (which is herein incorporated by reference), the present inventors genetically fused a gene encoding a streptavidin-binding peptide to an anti-VEE scFv antibody gene. In order to provide proper antecedent basis for the term "genetically biotinylated," the following construction example from 60/448,902 is incorporated:

Construction of p CRT7mA116SBP

The pPICZαBmA116 recombinant plasmid, containing anti-VEE mA116 scFv Ab gene, arranged in variable heavy (VH)-variable light (VL) chain orientation via $(Gly_4Ser)_3$ linker, was constructed previously. In order to introduce a SBP sequence PCHPQFPRCYA (Lue et at., 1998) followed by a 6His tag at the C-terminus of A116 scFv Ab, two complementary oligonucleotides corresponding to the SBP sequence and 6His tag with flanking sequences for restriction enzymes Not I and Sal I, were synthesized and purified by Life Technologies (Burlington, ON). The sequences were as follows: sense, 5'-ggccgcCCATTCTGGTGGTGGTG-GCCCATGCCATCCGCAGTTCCCACGATGTTAT GCGGGTGGTGGCGGTTCTCATCATCAT-CATCATCATTGAg-3' anti-sense, tcgacTCAATGATGAT-GATGATGATGAGAACCGCCACCACCCG-CATAACATCGT GGGAACTGCGGATGGCATGGGCCACCAC-CACCAGAATGGgc-3'. The two oligonucleotides were heated to denature, and then annealed to a single double-stranded oligonucleotide by slow cooling to room temperature. The annealed dimer possessed a Not I sticky end on one side and Sal I on the other side, and was ligated to pPICZαBmA116 that had been cut with Not I and Sal I. The resulting plasmid was named pPICZαBmA116SBP. To obtain high expression of the recombinant fusion protein, the PCR method was introduced to amplify the mA116 scFv/SBP/6His sequence in pPICZαBmA116SBP vector and the PCR product was subcloned into a T7 RNA polymerase-regulated expression vector. Two primers were synthesized on an Oligo 1000 DNA synthesizer (Beckman Instruments. Fullerton, Calif.). The sequence of the forward primer was 5'-ATGGCTAAAGAAGAAGGGGTATC-3' and the reverse was 5'-TCATGTCTAAGGCTACAAACTCAA-3'. PCR reaction in a 50 µl volume consisted typically of 200 µmol each dNTP, 0.6 µM primers, 0.1 µg template, and 1.25 unit of HotStarTaq™ DNA polymerase in buffer supplied by the manufacturer (Qiagen, Mississauga, ON). Initial activation (95° C. for 15 min) was carried out followed by cycling (94° C. for 1 min, 61° C. for 1 min and 72° C. for 2 min), repeated 30 times, on a Peltier Thermal Cycler (DNA Engine PTC-200; MJ Research, Watertown, Mass.). After gel-purification, the PCR fragment was cloned into the pCRT7 vector by use of a pCRT7 TA cloning expression kit in accordance with the manufacturer's instructions (Invitrogen, Carlsbad, Calif). The recombinant plasmid, named pCRT7mA116SBP, contained the correct orientation of the insert, mAl 16 scFv/SBP/6His tag, as confirmed by restriction digestion fragment mapping and DNA sequencing.

The resulting recombinant fusion antibody not only retained VEE antigen-binding specificity similar to that of the parental mAb, but also possessed streptavidin-binding activity. It would be advantageous to employ the genetically fused biotinylated scFv antibody, or genetically biotinylated scFv antibody, in the IFA/LAPS assay in order to obviate the disadvantages of using antibodies prepared by chemical biotinylation.

SUMMARY OF INVENTION

The present invention teaches the sensitivity of the IFA/LAPS assay for identification of VEE, when genetically biotinylated scFv (B-scFv) antibody is used. It also compares such sensitivity between the chemically biotinylated parental mAb and those which were genetically biotinylated.

It is an object of the present invention to investigate the precision, accuracy, and specificity of the IFA/LAPS assay incorporating genetically B-scFv antibody for the identification of VEE and to demonstrate that such assay is highly sensitive, specific, quantitative and reproducible.

It is another object of the present invention to show the potential for batch-to-batch variability resulting from inequality in the number of biotin molecules labeled per antibody molecule, when biotinylated chemically.

According to the invention, it provides a method for detecting VEE using a genetically B-scFv antibody, comprising: (a) reacting the genetically biotinylated scFv Ab with a sample containing VEE for observing antigen-binding activity; and (b) analyzing the reactant by a system consisting of an immunofiltration-enzyme assay with a light addressable potentiometric sensor.

BRIEF DESCRIPTION OF THE DRAWINGS

FIG. 2 shows standard curves for IFA/LAPS assay incorporating with biotinylated scFv (B-scFv) and fluoresceinated polyclonal Ab (F-pAb) in the detection of VEE.

DETAILED DESCRIPTION OF THE PREFERRED EMBODIMENT

Materials and Methods

Reagents and Solutions

Figure 1:
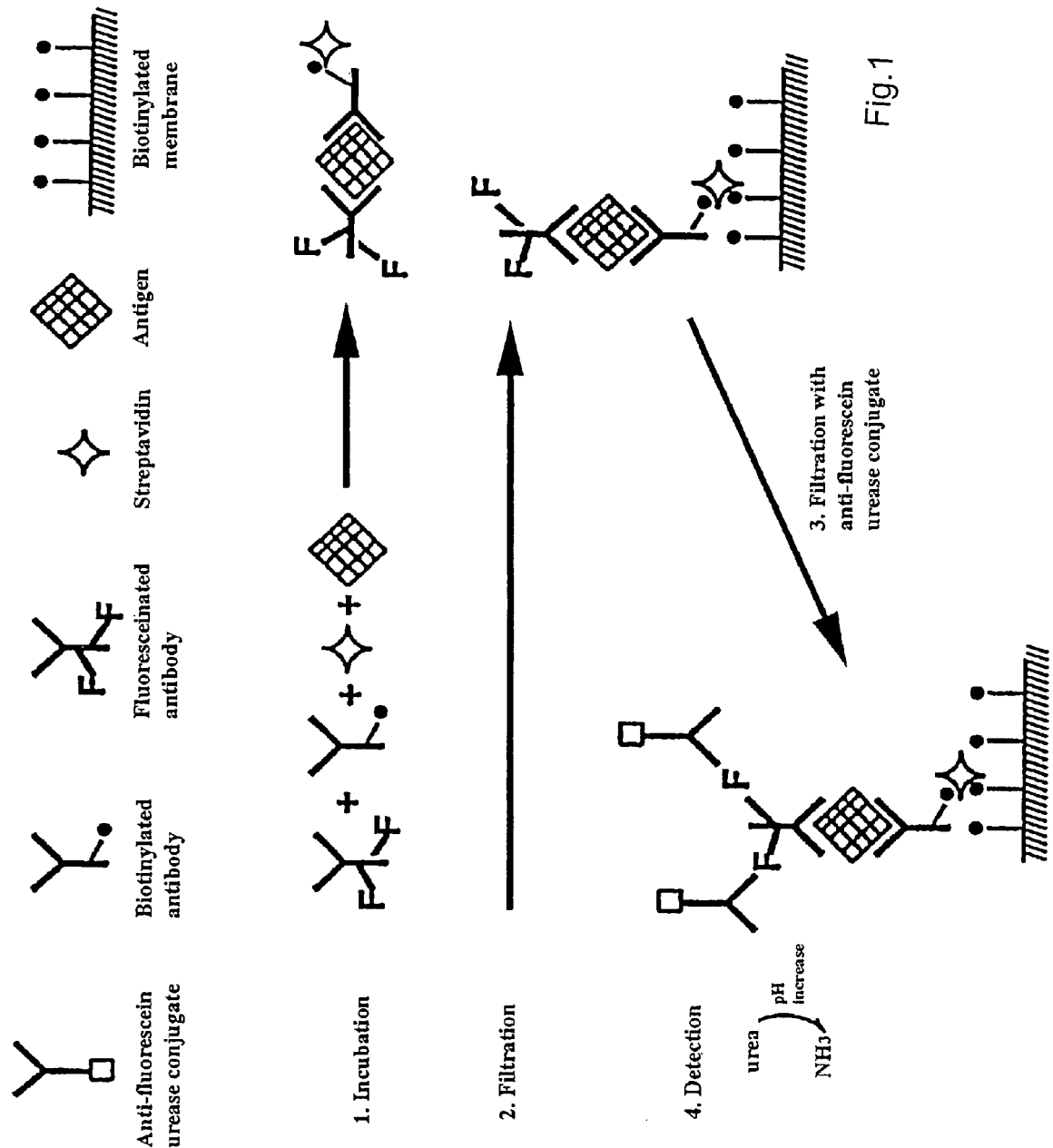
FIG. 1 is a schematic representation of the IFA/LAPS system.

Sodium dihydrogen phosphate ($NaH_2PO_4 \cdot 2H_2O$) and Triton X-100 were obtained from BDH Chemicals (Toronto, ON). Bovine serum albumin (BSA), sodium chloride (NaCl), sodium hydroxide (NaOH), Tween-20 and urea were obtained form Sigma-Aldrich Canada Ltd (Oakville, ON). Streptavidin was obtained from Scripps Laboratories (San Diego, Calif.). Biotinylated BSA-block nitrocellulose membrane sticks and antibody labeling reagents (N-hydroxysuccinimide esters of carboxyfluorescein and dinitrophenyl biotin) were purchased from Molecular Devices Corp (Menlo Park, Calif.). Anhydrous dimethylformamide (DMF) was purchased from Biolynx Inc (Brockville, ON). Sephadex G-25 columns were obtained from Amersham Pharmacia (Baie d'Urfé, QC). Washing buffer consisted of 10 mM $NaH_2PO_4$ (pH 6.5), 150 mM NaCl, and 0.05% Tween-20. Assay buffer consisted of 10 mM $NaH_2PO_4$ (pH 7.0), 150 mM NaCl, 0.025% Triton X-100, and 0.1% BSA. The substrate solution was 100 mM urea in the wash buffer (pH 6.5).

Viruses

VEE strain TC-83 and Western equine encephalitis virus (WEE) strain B11 were prepared as follows. Viruses were cultured in Vero monkey kidney cells or in baby hamster kidney cells (America Type Culture Collection, Rockville, Md.). Cells were maintained in complete Dulbecco Minimum Essential Medium (DMEM) (Invitrogen Canada Inc., Burlington, ON) containing 5% fetal calf serum. When cells were confluent, the medium was decanted and replaced by a volume of virus inoculum, in DMEM, sufficient to just cover the monolayer. The virus inoculum was spread over the monolayer every 15 min and was allowed to adsorb to the cells for a total of 1 hr. Fresh complete medium was added and the flasks were incubated for several days to one week. When 90% cytopathic effect was reached, cells and medium were harvested and centrifuged at 10,000 g for 30 min. To the pooled supernatants, polyethylene glycol (~6,000 MW) (7% final concentration) and NaCl (2.3% final concentration) were added and the mixtures were allowed to incubate with stirring for 15-20 hours at 4° C. The mixtures were then centrifuged at 10,000 g for 30 min and the resulting supernatants discarded. The virus pellet was resuspended in a small volume of phosphate buffered saline (PBS) and stored at −70° C. to await purification. The virus particles were purified by sucrose density gradient centrifugation by standard techniques. Samples were centrifuged at 100,000 g at 4° C. for 3.5 hr. Fractions containing virus were pooled and the pooled virus was dialyzed against PBS. Protein concentration of the purified virus was determined by protein assay and virus purity was assessed by polyacrylamide gel electrophoresis.

Antibodies

Genetically biotinylated scFv antibody to VEE was constructed from mAb 1A4A1 to VEE, expressed in bacteria and purified in accordance with the method disclosed in U.S. Provisional Application No. 60/448,902. The hybridoma cell line producing 1A4A1 mAb was provided by Dr. J. T. Roehrig (Division of Vector-borne Infectious Diseases, Centers for Disease Control and Prevention, Fort Colins, Colo.). MAb 1A4A1 was purified from vectraCell™ bioreactor (BioVectra™ Diagnostic Chemicals Ltd., Charlottetown, Prince Edward Island) cultures using protein G affinity chromatography (Biolynx Inc.). Polyclonal antibody (pAb) to VEE was purified from rabbit serum using protein G affinity chromatography. Anti-fluorescein urease conjugate was purchased from Molecular Devices Corp.

Instrumentation

The LAPS used in the present invention was the Threshold™ Unit marketed by Molecular Devices Corp. The instrument was controlled by a computer and Threshold™ version 2 software. Reactions took place on membrane sticks (Molecular Devices Corp.) and the Threshold™ Unit could process a maximum of four membrane sticks simultaneously (eight reaction test spots per stick). Assay time was less than 2 hours.

Preparation of Biotinylated mAb and Fluoresceinated pAb

Biotinylated mAb (B-mAb) and fluoresceinated pAb (F-pAb) were prepared according to procedures outlined in the Threshold™ manual. Briefly, antibodies were adjusted to 1 mg/ml in PBS. MAb 1A4A1 was biotinylated chemically via N-hydroxysuccinimide ester of dinitrophenyl biotin (reconstituted in DMF) for 2 hours at room temperature; the molar coupling ratio (MCR) of biotin hapten to antibody was 10:1. The pAb was fluoresceinated via N-hydroxysuccinimide ester of carboxyfluorescein (reconstituted in DMF) for 2 hours at room temperature; the MCR of fluorescein hapten to antibody was 20:1. Unreacted haptens were removed using PD-10 columns (Amersham Pharmacia Biotech) equilibrated in PBS. The number of moles of hapten covalently bound per mole of antibody was determined for each conjugate using the molar incorporation ratio (MIR) described in the Threshold™ manual. The MIRs of B-mAb and F-pAb were 3.8 and 4.0, respectively. The labeled antibodies were stored at 4° C. until used.

Assay Procedure

The IFA/LAPS scheme for the Threshold™ unit is depicted in FIG. 1.

A volume of 100 µl of VEE (0-20 µg/ml) was incubated with 100 µl of genetically biotinylated scFv (B-scFv) or B-mAb (1-5 µg/ml) and 100 µl of F-pAb (1-5 µg/ml) at room temperature for 30 min. At the end of the incubation period, 100 µl (5 µg/ml in assay buffer) streptavidin was added to the reaction mixture and mixed thoroughly. The resulting mixtures were filtered through the membrane sticks (mounted in filter bases) on the Threshold™ Unit under low vacuum (complete filtration in ~10 min). The sticks were washed with 2 ml wash buffer while filtering under high vacuum (complete filtration in ~8 min). One ml of anti-fluorescein urease conjugate was then added to the membrane sticks and filtered under low vacuum, followed by the addition of 2 ml of wash buffer and filtration under high vacuum. The membrane sticks were removed from the filtration compartment, and inserted into the reader chamber containing the LAPS and the substrate solution, urea. The pH change with respect to time at the surface of the sensor was monitored as the rate of change of the surface potential with respect to time in μV/sec. The rate of pH change depends on the number of urease-containing antibody-antigen sandwiches immobilized on the membrane stick during the filtration capture process.

Protein Assay

Virus protein concentration was estimated spectrophotometrically with a micro BCA protein assay kit purchased from Biolynx Inc.

Results

Optimal Ratio Between B-scFv or B-mAb and F-pAb for Detection of VEE

A preliminary assay was first performed using a range of VEE concentrations (10 to 2,000 ng/spot) and antibody concentrations (ng/spot) in the following B-scFv/F-pAb ratios: 200:200, 200:100, 100:200, and 100:100. From the preliminary result, a VEE concentration of 500 ng/spot, providing a mid-range LAPS signal was chosen for further experiments. A series of IFA/LAPS experiments was performed to investigate the effect of the ratios of B-scFv and F-pAb on the output response of the assay. The aspect of the response of interest was the signal to noise ratio (S/N). S represented the output of LAPS from VEE. N was the background of the assay, that is, the output of the LAPS for the reagents without VEE. The S/Ns obtained using varying B-scFv/F-pAb concentrations (ng/spot) with a constant concentration of VEE antigen (500 ng/spot) were determined (Table 1). The B-scFv/F-pAb ratio giving the highest S/N was found to be 250:500 (ng/spot). Similar experiments were performed to determine the optimal concentration ratios of B-mAb and F-pAb. The B-mAb to F-pAb concentration ratio giving the highest S/N with fixed concentration of VEE was, similarly, found to be 250:500 (ng/spot) (Table 1).

Standard Curve and Sensitivity

Figure 2:
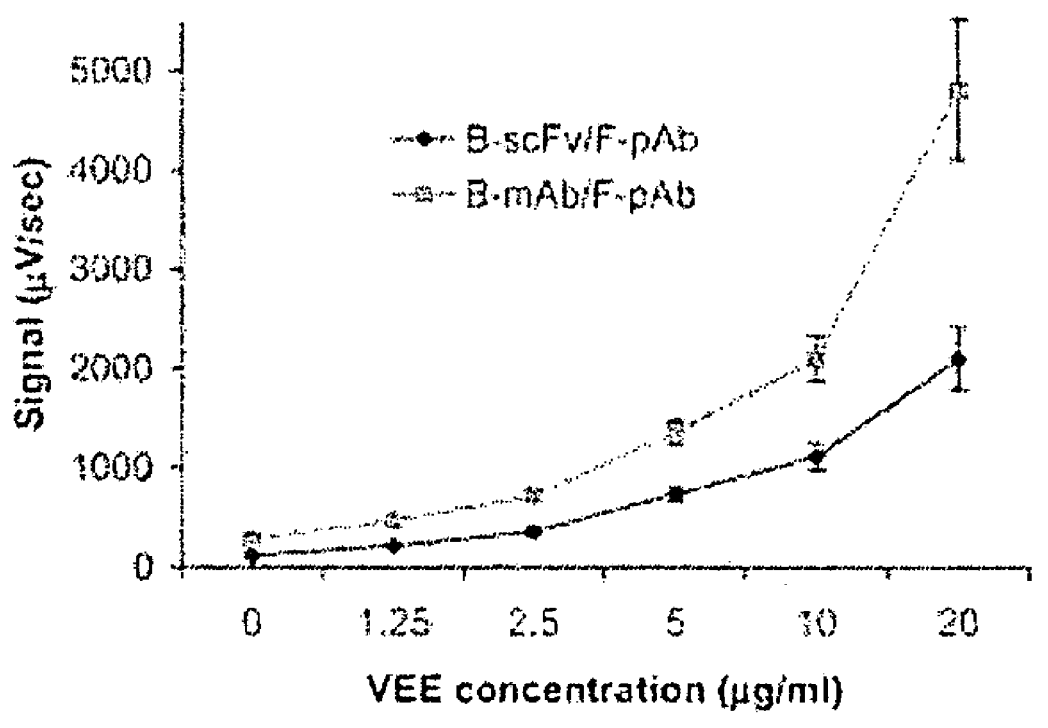

To prepare IFA/LAPS standard antigen concentration curves, two-fold serial dilutions of VEE ranging from 125 to 2,000 ng/spot (1.25 to 20 μg/ml) in assay buffer were titrated using optimal ratios of B-scFv or B-mAb and F-pAb (250:500 ng/spot) (FIG. 2).

Assay sensitivity, or limit of detection (LOD), was defined as the lowest concentration of VEE producing an output signal greater than the background plus three standard deviations of the background, i.e., the lowest concentration that could be measured accurately and precisely. The LOD of the IFA/LAPS incorporating B-scFv for detection of VEE was 0.29 μg/ml, while that incorporating B-mAb was 0.34 μg/ml.

Assay Precision

Intra- and inter-assay variabilities were evaluated by testing three different VEE concentration samples (20, 5, and 1.25 μg/ml) in six assays performed together on the same day and on 6 different days, respectively. Intra- and inter-assay coefficients of variation for the precision were determined by the ratios of standard deviations and means from six assays. These ranged from 15 to 19% and 18%, respectively (Tables 2 and 3).

Assay Accuracy

Figure 3:
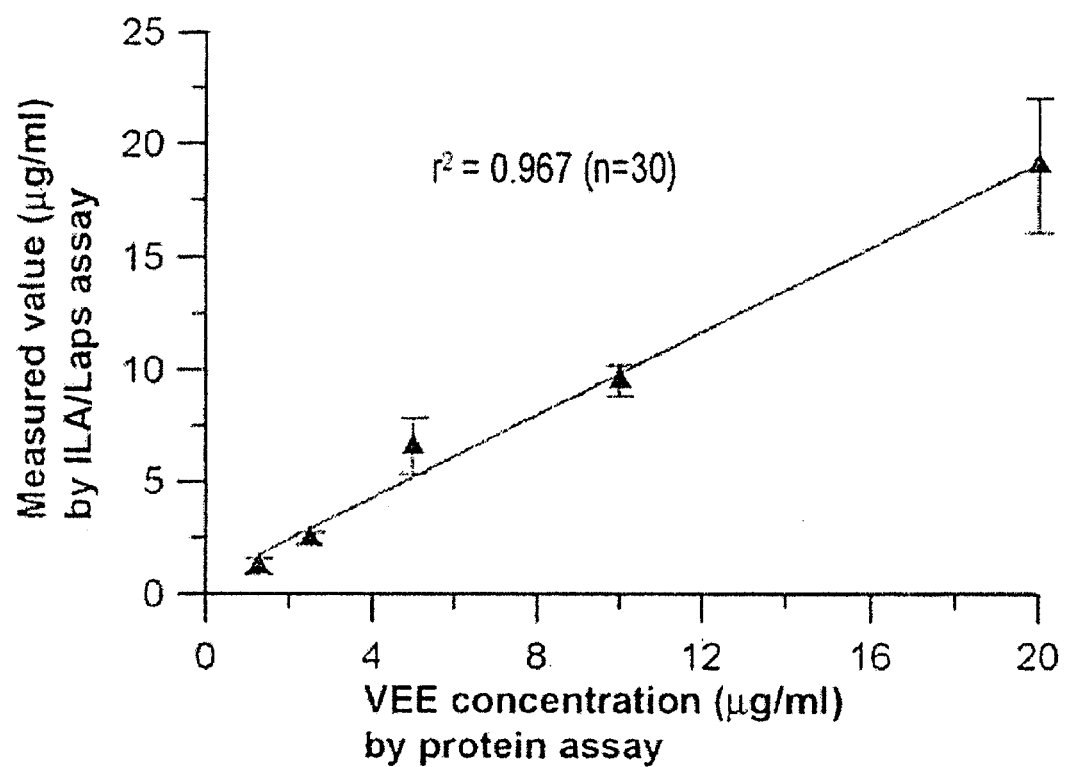
FIG. 3 shows quantitation of VEE by IFA/LAPS assay incorporating B-scFv. Each data point represents the mean (n=6) of an independent determination of VEE concentration.

The IFA/LAPS system incorporating B-scFv was assessed for accuracy in quantitation of VEE by comparing the protein concentrations measured by protein assay with the protein concentrations estimated by the IFA/LAPS standard curve. For five different test samples in which concentrations of VEE were estimated by protein assay to be in the range of 1.25-20 μg/ml, the mean difference between protein concentrations estimated by protein assay and by IFA/LAPS standard curve was about 10%. A linear regression analysis relating protein concentration estimated by protein assay with protein concentration measured by IFA/LAPS yielded a high correlation ($r^2=0.967$) (FIG. 3).

Assay Specificity

The specificity of the IFA/LAPS assay incorporating B-scFv was evaluated by challenging the assay with one other member of the alphavirus genus of the family *Togaviridae*, WEE. The results showed no cross-reaction in the assay between VEE and WEE (data not shown).

Discussion

The present invention applies genetically biotinylated scFv antibody against VEE in a commercially available assay system employing IFA/LAPS for rapid detection of VEE. The invention demonstrates the feasibility of replacing a murine mAb, biotinylated chemically, with a scFv antibody, biotinylated genetically, as immunodiagnostic reagent in the IFA/LAPS system to detect VEE.

Before comparing the sensitivity of assays incorporating B-scFv and B-mAb in the IFA/LAPS system for detection of VEE, optimization of the concentration ratios of B-scFv or B-mAb and F-pAb was investigated and identified. These ratios are influenced by the type and affinity of the antibodies and are important aspects of the assay. Optimizations of assay conditions such as buffer formulation, temperature, incubation time, etc., were not undertaken as these had been previously determined and were available in the Threshold™ manual. It was found that the optimal concentration ratios of both B-scFv and B-mAb and F-pAb were 250:500 (ng/spot). By using these concentration ratios, a standard curve relating IFA/LAPS signal and VEE concentration was constructed. Although signals in the IFA/LAPS assay incorporating B-mAb were two-fold higher than in the assay incorporating B-scFv, the background noise in the assay using B-mAb was twice as high as in the assay using B-scFv, resulting in similar LODs whether B-scFv or B-mAb were used. The LOD with B-scFv was 0.29 μg/ml, while that with B-mAb was 0.34 μg/ml. These results indicated that genetically biotinylated scFv could replace chemically biotinylated mAb in the IFA/LAPS system. As disclosed in U.S. Provisional Application No. 60/448,902, it had been shown that the sensitivity of an enzyme-linked immunosorbent assay (ELISA) incorporating B-scFv and horseradish peroxidase (HRP)-conjugated streptavidin to detect VEE was about 0.2 μg/ml, a LOD value comparable to that obtained in the IFA/LAPS system incorporating B-scFv. The IFA/LAPS system however, has advantages over ELISA in that the IFA/LAPS assay system requires less time and effort to perform.

The present invention also investigated the precision, accuracy, and specificity of the assay in order to further evaluate the IFA/LAPS system incorporating B-scFv. A standard curve relating protein concentration to IFA/LAPS signal was used to accurately assess the concentration of VEE. Protein concentration, whether estimated by IFA/LAPS standard curve or by protein assay, differed by no more than 10%. Intra-assay and inter-assay precision varied by less than 20%. In addition, the specificity of the assay was confirmed by showing no cross-reactivity with WEE, a virus with a genetic background and a disease spectrum very similar to that of VEE.

In conclusion, the IFA/LAPS incorporating B-scFv was shown to be accurate, precise, reliable, reproducible, and sensitive for use in measuring VEE. More importantly, use of this assay obviates the need for chemical biotinylation of antibody, which often results in potential impairment of the antibody antigen-binding site and batch-to-batch differences in degree of labeling.

It is to be understood that the embodiments and variations shown and described herein are merely illustrative of the principles of this invention and that various modifications may be implemented by those skilled in the art without departing from the scope and spirit of the invention.

In addition, the List of Prior Art Literatures referred to in the Background of the Invention section is incorporated by reference herein.

TABLE 1

Effects of concentration ratios of B-scFv or B-mAb and F-pAb on S/Ns of IFA/LAPS assays to detect VEE

| B-scFv/F-pAb (ng/spot) | S/N ($\mu$V/s) | B-mAb/F-pAb (ng/spot) | S/N ($\mu$V/s) |
|---|---|---|---|
| 125:500 | 5.63 | 125:500 | 6.37 |
| 250:500 | 8.78 | 250:500 | 7.60 |
| 500:500 | 4.80 | 500:500 | 3.18 |
| 125:250 | 5.82 | 125:250 | 6.11 |
| 250:250 | 6.50 | 250:250 | 5.22 |
| 500:250 | 4.51 | 500:250 | 4.86 |
| 125:125 | 3.43 | 125:125 | 3.89 |
| 250:125 | 5.14 | 250:125 | 5.02 |
| 500:125 | 4.70 | 500:125 | 3.38 |

Samples were tested in replicates of four.

TABLE 2

Intra-assay precision of IFA/LAPS assay incorporating B-scFv to detect VEE

| VEE ($\mu$g/ml) | N | Mean ($\mu$V/sec) | Standard deviation ($\mu$V/sec) | Coefficient of Variation (%) |
|---|---|---|---|---|
| 20 | 6 | 2156 | 309 | 15 |
| 5 | 6 | 844 | 160 | 19 |
| 1.25 | 6 | 243 | 38 | 16 |

The intra-assay precision was determined from the results of six replicates performed together on the same day for each VEE concentration.

TABLE 3

Inter-assay precision of IFA/LAPS assay incorporating B-scFv to detect VEE

| VEE ($\mu$g/ml) | N | Mean ($\mu$V/sec) | Standard deviation ($\mu$V/sec) | Coefficient of Variation (%) |
|---|---|---|---|---|
| 20 | 6 | 2076 | 370 | 18 |
| 5 | 6 | 918 | 175 | 18 |
| 1.25 | 6 | 240 | 43 | 18 |

The inter-assay precision was determined from the results of six assays performed on different days for each VEE concentration.

What is claimed is:

1. A method for detecting Venezuelan equine encephalitis virus ("VEE") using a genetically biotinylated single chain fragment variable antibody ("scFv Ab"), comprising:
   (a) reacting the genetically biotinylated scFv Ab with a sample containing VEE for observing antigen-binding activity; and
   (b) analyzing the reactant by a system consisting of an immunofiltration enzyme assay ("IFA") with a light addressable potentiometric sensor ("LAPS").

2. The method of claim 1, wherein said genetically biotinylated scFv Ab is a genetically biotinylated streptavidin-binding peptide tagged recombinant scFv Ab.

3. The method of claim 2, wherein said genetically biotinylated scFv Ab has streptavidin-binding activity.

4. The method of claim 2, wherein said IFA assay comprises the steps of:
   (a) preparing an immunocomplex sandwich, said sandwich consisting of VEE, genetically biotinylated antibody, fluoresceinated polyclonal antibody and streptavidin;
   (b) capturing said sandwich by filtration on biotinylated membrane; and
   (c) detecting said captured sandwich by anti-fluorescein urease conjugate.

5. The method of claim 4, wherein a concentration ratio of genetically biotinylated antibody to fluoresceinated polyclonal antibody is 250:500 (ng/spot).

* * * * *